United States Patent [19]

Fukazawa et al.

[11] Patent Number: 5,232,923

[45] Date of Patent: Aug. 3, 1993

[54] CATECHOL DERIVATIVES AND PHARMACEUTICAL PREPARATIONS CONTAINING SAME

[75] Inventors: Nobuyuki Fukazawa, Yokohama; Kengo Otsuka, Kamakura; Shimada Shizuo, Mobara; Yukio Miyama, Chiba; Fumiaki Ikeda, Mobara; Tatsuo Kaiho, Chiba, all of Japan

[73] Assignee: Mitsui Toatsu Chemicals, Incorporated, Tokyo, Japan

[21] Appl. No.: 689,098

[22] Filed: Apr. 22, 1991

Related U.S. Application Data

[63] Continuation of Ser. No. 321,138, Mar. 9, 1989, abandoned.

[30] Foreign Application Priority Data

Mar. 18, 1988 [JP] Japan .................................. 63-63515
Mar. 18, 1988 [JP] Japan .................................. 63-63516
Aug. 15, 1988 [JP] Japan .................................. 63-201865
Aug. 15, 1988 [JP] Japan .................................. 63-201866

[51] Int. Cl.⁵ ................ A61K 31/535; C07D 295/104
[52] U.S. Cl. ................ 514/237.5; 514/255; 514/330; 514/423; 544/171; 544/173; 544/386; 546/226; 548/540
[58] Field of Search .............. 548/540; 546/226; 544/171, 173, 386; 514/237.5, 255, 330, 423

[56] References Cited

U.S. PATENT DOCUMENTS

| | | | |
|---|---|---|---|
| 4,181,738 | 1/1980 | Ginos et al. | 424/330 |
| 4,529,604 | 7/1985 | Kaiser et al. | 514/654 |
| 4,639,452 | 1/1987 | Platel et al. | 544/386 |
| 4,824,842 | 4/1989 | Nakamuya et al. | 514/237.5 |

FOREIGN PATENT DOCUMENTS

| | | |
|---|---|---|
| 0089710 | 9/1983 | European Pat. Off. |
| 0261977 | 3/1988 | European Pat. Off. |
| 3740383 | 1/1988 | Fed. Rep. of Germany |
| 0162672 | 7/1988 | Japan .................. 548/540 |

OTHER PUBLICATIONS

Kellogg, C. Chemical Abstracts vol. 85, No. 5 Abstract No: 29135p Aug., 1976.
Wistrand, L. Chemical Abstracts vol. 108, No. 17 Abstract No: 150247y Apr., 1988.
Hoelzel, C. Chemical Abstracts vol. 101, No. 15 Abstract No: 127835g Oct., 1984.
Stine, S. Chemical Abstracts vol. 96, No. 17 Abstract No: 140748g Apr., 1982.
Boissier et al. Arch. int. Pharmacodyn., 1965 158, No. 1 Action De La Cafeine Sur La Motilite Spontanee De La Souris.
Furukawa et al., J. Neurochemistry, 40, 734–744 (1983) "Highly Sensitive Enzyme Immunoassay for . . . Growth Factor".
Taniuchi et al., Proc. Natl Acad Sci USA, 83, 1950–1954 Mar. 1986 "Nerve growth factor . . . in rat brain".
Furukawa et al., J. Biol Chem vol. 261, No. 13, May 1986 6036–6047 "Catecholamines Induce . . . L-M Cells".
Shelton et al., Proc Natl Acad Sci USA, 83, 2714, Apr 1986 "Studies on the expression of . . . population neurons".
Whittemore et al., Proc Natl Acad Sci, 83, 817–821 Feb. 1986 "Developmental and regional expression of . . . nervous system".
Shelton et al., Proc. Natl Acad Sci USA 81, 7951–7955, Dec. 1984 "Expression of the β-nerve growth factor gene . . . effector organs".

(List continued on next page.)

*Primary Examiner*—Joseph Paul Brust
*Assistant Examiner*—Jacqueline Haley
*Attorney, Agent, or Firm*—Nixon & Vanderhye

[57] ABSTRACT

Catechol derivatives which produce nerve growth factor in particular tissues of the brain are disclosed. These derivatives provide preventive and therapeutic effects for regressive disorders of the central nervous system including senile dementia of the Alzheimer type.

9 Claims, No Drawings

OTHER PUBLICATIONS

Korsching et al., Proc. Natl Acad Sci USA 80, 3513-3516 Jun. 1983 "Nerve growth factor in sympathetic ganglia . . . innervation".

Yankner et al., Ann Rev Biochem 51, 1982 845-868 "The Biology and Mechanism of Action of Nerve Growth Factor".

Furukawa et al., FEBS 4216 Letters, 208, 258-262 Nov. 1986 "Aliphatic side chain of catecholamine . . . growth factor".

Furukawa et al., Biochem Biophy Res Comm, 142, 395-402 Jan. 1987 "Synthesis/secretion of nerve growth . . . astroglial cells".

Furukawa et al., Biochem Biophy Res Comm, 147, 1048-1054 Sep. 1987 "Regulation of Nerve Growth Factor Synthesis . . . Astroglial Cells".

Furukawa et al., Biochem Biophys Res Comm, 136, 57-63, Apr. 1986 "Synthesis and Secretion of Nerve Growth Factor . . . in Culture".

Furukawa et al., FEBS Letters, 208, 258-262, Nov. 1986 "Aliphatic side chain of catecholamine . . . growth factor".

Furukawa et al., J. Biol Chem., 261, 6039-6047 "Catecholamines Induce an Increase in Nerve Growth Factor . . . L-M Cells" (1986).

Imura et al., Natural Product & Biological Activities, 1986 "Synthesis . . . in Culture" Naito Found Symposium U. of Tokyo Press.

Furukawa et al., J. Biol Chem, 259, 1259-1264 (1984) "Nerve Growth Factor . . . Cells in Culture".

Thonen et al., Physiological reviews vol. 60, No. 4, Oct. 1980 1284-1335 "Physiology of Nerve Growth Factor".

Heumann et al., EMBO Journal vol. 3 No. 13, 3183-3189 (1984) "Relationship between levels . . . peripheral target tissues".

S. Korsching et al., EMBO Journal vol. 4, No. 6, 1389-1393 (1985) "Levels of nerve growth factor . . . cholinergic innervation".

Schwab et al., Brain Research 168. (1979) 473-483 "Nerve Growth Factor (NGF) . . . and substantia nigra".

Seiler et al., Brain Research 300 (1984) 33-39 "Specific Retrograde of Nerve Growth Factor . . . in the Rat".

Perry et al., The Lancet, 189 Jan. 1977 p. 189 "Necropsy Evidence of Central . . . Senile Dementia".

Whitehouse et al., Annals of Neurology 10, 122, (1981) "Alzheimer Disease . . . Nucleus Basalis".

Flicker et al., Pharm Biochem & Behavior vol. 18, 973-981 (1983) "Behaviorial and Neurochemical Effects . . . in the Rat".

Goedert et al., Molecular Brain Research 1 (1986) 85-92 "Nerve Growth Factor . . . Alzheimer's Disease".

CATECHOL DERIVATIVES AND PHARMACEUTICAL PREPARATIONS CONTAINING SAME

This is a continuation of application Ser. No. 07/321,138, filed Mar. 9, 1989, now abandoned.

BACKGROUND OF THE INVENTION

1. Field of the Invention

The present invention relates to catechol derivatives and their use as medicines. More particularly, it relates to catechol derivatives having the ability to induce production and secretion of nerve growth factor (hereinafter abbreviated as NGF) in the local tissue of the brain. The invention also relates to prophylactic and therapeutic preparations containing these derivatives as active ingredients for regressive disorders of the central nervous system.

2. Description of the Prior Art

Basic and clinical researches have been intensively promoted in order to establish early diagnosis and etiologic therapy for various senile diseases with the increasing average span of life in the world. Regressive disorders of the central nervous system are also one of the principal research subjects. Senile Dementia of the Alzheimer Type (hereinafter abbreviated as SDAT), also known as Alzheimer Disease, a typical disease in particular, is becoming a serious social problem as a result of its increase primarily in advanced countries as well as the progressive and tragic course of the disease.

Particularly in recent years, many researchers and clinicians have investigated extensively and yet neither fundamental elucidation of the disease nor effective early diagnosis and therapy have been established. Many pathological findings, however, have been accumulated on the direct cause of failure of immediate memory and disorientation which are characteristic early symptoms of SDAT. According to these findings, the cause is a progressive degeneration in magnocellular cholinergic tracts projecting from the basal forebrain into the cerebral cortex and hippocampus which are the centers of memory and learning, and an accompaning dysfunction in this responsible region. In addition, precursors in acetylcholine biosymthesis or inhibitors of choline esterase were actually administered to SDAT patients as an activation treatment for the brain cholinergic neuron. Cases of partial improvement have been reported whereas generally the results have been not as effective as expected.

NGF has been the subject of many studies since its discovery by R. Levi-Montalcini and S. Cohen et al. It has already been demonstrated by several experiments in physiological chemistry that NGF is an essential factor for the peripheral nervous system relating to differentiation and growth of sensory and sympathetic nerves in the fetus and further, to the survival and maintenance of functions in the sympathetic neurons of an adult.

NGF, however, is a potent biologically active substance even in ultra trace amounts. In spite of long term studies, precise information has not been obtained on its distribution in the tissue and movement which directly prove vital functions. Most recently, development and improvements have been made using the highly sensitive enzyme linked immunosorbent assay (hereinafter abbreviated as ELISA) to identify the active subunit of NGF, e.g. $\beta$-NGF (hereinafter simply referred to as NGF). Thus satisfactory detection-sensitivity and specificity for this examination have been attained [S. Furukawa et al., J. Neurochem., 40, 734–744 (1983); S. Korshing and H. Thoenen, Proc. Natl. Acad. Sci. U.S.A., 80, 3513–3516 (1983)].

Further, the NGF gene has been cloned and structure is analyzed. A method for determining messenger RNA (hereinafter abbreviated as m RNA) for $\beta$-NGF has been established using its complementary DNA (hereinafter abbreviated as cDNA) as a probe [D. L. Shelton and L. F. Reichardt, Proc. Natl. Acad. Sci. U.S.A., 81, 7951–7955 (1984); R. Heumann et al., EMBO J., 3, 3183–3189 (1984)].

By applying these procedures, a clear positive correlation has been demonstrated between the grade of sympathetic innervation in the peripheral nervous system and gene expression of NGF in the innervated tissue.

More surprisingly, NGF has also been detected in the central nervous system of rats, particularly in hippocampus, neocortex, and basal forebrain, e.g. septum, olfatory bulb, diagonal band of Broca, and nucleus basalis magnocellularis. In addition, its mRNA content has been found at a high level in the hippocampus and neocortex. On the other hand, the NGF content in the septum of the basal forebrain has been found at a low level as in other regions of the brain where no NGF antigen was detected [S. Korshing et al., EMBO J., 4, 1389–1393 (1985)]. Thereafter the results have been successively traced by other research groups [D. L. Shelton and L. F. Reichardt, Proc. Natl. Acad. Sci. U.S.A., 83, 2714–2718 (1986); S. R. Whittemore et al., Proc. Natl. Acad. Sci. U.S.A., 83, 817–821 (1986)].

According to these results, the NGF gene is expressed not only in the peripheral nervous system, but in the central nervous system as well. Furthermore, it was demonstrated that NGF is produced and secreted in the innervating regions of the chlorinergic tracts projecting from the origins of the basal forebrain to the neocortex and hippocampus, the centers of memory and learning, and then taken up at the nerve endings and transported in a retrograde manner through axons to reach somata in the origins. NGF has already been proven by a series of physiological experiments to be an essential factor for the survival and maintenance of functions in the chlorinergic tracts. These results have demonstrated the assumption that NGF has a specific function as a "neurotropic factor" also in the central nervous system. Thereafter the experiment has been traced by several research groups and has also been proven by investigation of NGF receptors and their distribution in the brain.

The present inventors have investigated the function of NGF as the neurotropic factor in the central nervous system. As discussed in the literature, summarized above, the disorders in memory and learning which are the early symptoms of SDAT are directly caused by the progressive degeneration of cholinergic tracts and consequent dysfunction of brain domains under their control.

The inventors, however, now believe that the failure of production and secretion of NGF in particular regions of brain can be the truly fundamental cause of early symptoms in SDAT. This is because conventional symptomatic trials against SDAT, such as supplementation and/or availability improvement therapies with acetylcholine, have been made without any remarkable result. On the other hand, it is believed that effective therapy may be realized if the functionally vicious cycle between responsible nerves and regions under their control could be broken by maintaining the production and secretion of NGF in the cerebral cortex and hippocampus.

Procedures for preparing human-type β-NGF in a large amounts have already been developed by gene-manipulation, yet many pharmacological and pharmaceutical limitations still exist on achieving supplemental therapy of NGF itself, which is a protein having a molecular weight of above 10,000. To date, there has been no application of NGF to the central nervous system.

It is important from the above viewpoint to investigate low molecular weight compounds capable of inducing the production and secretion of NGF in particular tissues to be used as therapeutics for substantial and effective supplemental NGF therapy. The present inventors have already reported catechol derivatives having such activity (Ikeda: U.S. patent application Ser. No. 07/098554). There are also reports of Furukawa et al. [Y. Furukawa et al., J. Boil. Chem., 261, 6039 (1986) and FEBS Letters, 208, 258(1986)]

SUMMARY OF THE INVENTION

The object of this invention is to provide a medicine capable of inducing the production and secretion of NGF in particular tissues as a substantial and supplemental NGF therapy. That is, to provide a compound having, in regions under the control of specific nerves, acrivity for promoting the production and secretion of NGF which functions as a "neurotropic factor" for the responsible nerves to be administered by usual and convenient method. The compound is administered as it is or as a modified compound in accordance with customary pharmacological and pharmaceutical considerations. It is believed that the compound increases the supplied quantity of NGF into the locus of degenerated nerves and enables these nerves to recover their function. In particular, the compound is usuful for the treatment of SDAT, a disorder in of central nervous system for which fundamental therapy has not yet provided.

In the early onset stage of the SDAT symptoms, peripheral administration of the catechol derivative can enhance the NGF production and secretion ability in the cerebral cortex and hippocampus regions of the central nervous system. The progress of characteristic degeneration in the responsible cholinergic neuron is thereby inhibited. Repair of damaged neurons and reinnervation by surviving neurous are thus promoted.

Therefore this invention provides significant new therapy according to a new mechanism of action depending upon brain plasticity.

The present inventors have investigated low molecular weight compounds capable of inducing the production and secretion ability of NGF in specific tissue. As a result, it has been found that a specific class of catechol derivatives have activity for inducing the production and secretion ability of NGF, and are effective to inhibit the progression and for therapy of regressive disorders of the central nervous system.

One aspect of this invention is a novel catechol derivative, or a pharmaceutically acceptable salt thereof, represented by the formula (I):

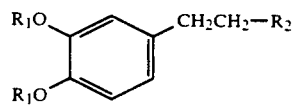

wherein $R_1$ is a hydrogen atom or an acetyl group and $R_2$ is a

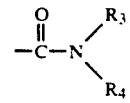

group or a

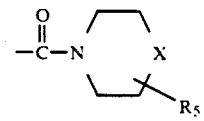

group, where $R_3$ and $R_4$ are each independently a hydrogen atom, alkyl group, cycloalkyl group, aryl group or a substituted aryl group, wherein except for sixteen combinations in $R_3$ and $R_4$, each member is a hydrogen atom or an alkyl group having one to three carbon toms, and wherein $R_5$ is a hydrogen atom, alkyl group, aryl group, substituted aryl group or an alkoxycarbonyl group, and X is a direct bond, oxygen atom, nitrogen atom or a methylene group.

Another aspect of this invention is prophylactic or therapeutic pharmaceutical preparation for the treatment of regressive disorders of the central nervous system which comprises as the active ingredient a catechol derivative represented by the formula (II):

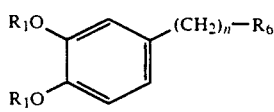

wherein $R_6$ is a

group,

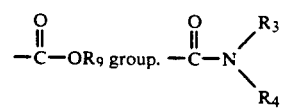

group, or a

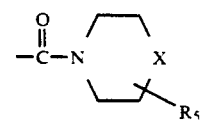

group, where $R_1$, $R_5$ and X are the same as above, and $R_3$ and $R_4$ are each independently a hydrogen atom, an alkyl group, cycloalkyl group, aryl group or a substituted aryl group and $R_7$ and $R_8$ are each independently a hydrogen atom, a lower alkyl group or a lower alkanoyl group and $R_9$ is a hydrogen atom or a lower alkyl group, and n is an integer of 1, 2 or 3, wherein except when $R_1$, $R_7$ and $R_8$ are hydrogen atoms and n is an integer of 2 and when $R_1$ and $R_7$ are hydrogen atoms, $R_8$ is a methyl group and n is an integer of 2.

DETAILED DESCRIPTION OF THE PREFERRED EMBODIMENT

As examples of the substituent in the catechol derivative represented by the formulas (I) and (II) of this invention, the alkyl group includes straight chain alkyl groups such as a methyl group, ethyl group, propyl group, butyl group, hexyl group, octyl group, decyl group, lauryl group, hexadecyl group, and a stearyl group, or branched chain alkyl groups such as an isopropyl group and an isobutyl group; the cycloalkyl group includes a cyclopropyl group, cyclobutyl group, cyclopentyl group, cyclohexyl group, and a cycloheptyl group; the aryl group includes a phenyl group and a naphthyl group; the substituted aryl group includes a benzyl group, phenethyl group, p-methylphenyl group and a o-methylphenyl group; the alkoxycarbonyl group includes a methoxycarbonyl group and an ethoxycarbonyl group; the lower alkyl group includes a methyl group, ethyl group and a propyl group; and the lower alkanoyl group includes a formyl group, acetyl group, propionyl group and a butyryl group.

Practical examples of the substituent having the formula (III):

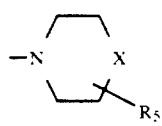

(III)

which is a part of the chemical structures represented by the formulas (I) and (II) are preferably a piperidino group, morpholino group, piperazino group, pyrrolidino group, 4-methylpiperazino group, 4-benzylpiperazino group, 4-diphenylmethanepiperazino group, prolyl group, nipecotinyl group and an isonipecotinyl group.

The method for preparing the compound of this invention will hereinafter be described.

Those known compounds among the compounds of this invention can be prepared by conventional methods. They are referred to as compound numbers 1-83 below. The desired compound of this invention can be readily prepared using conveniently available reactants such as dopamine, epinine and dihydrocaffic acid, and conducting chemical treatments such as the usual alkylation, acylation, esterification and conversion to amide (hereinafter as amidation). Novel compounds are prepared by the following methods.

In the first method, easily available dihydrocaffic acid ethyl ester is condensed by heating with the corresponding amine. The heating range is from room temperature to 200° C., and in many cases, the reaction can proceed without a solvent. The reaction may be carried out, if necessary, by using the corresponding amine in excess or in inert solvents such as toluene and xylene.

In the second method, easily available dihydrocaffeic acid is converted to the diacetyl derivative by a normal method using acetic anhydride or acetyl chloride, and further reacted with thionyl chloride. The corresponding acid chloride thus obtained is then reacted with the corresponding amine in the presence of a base. The base which may be used is an organic base such as pyridine and triethylamine, an inorganic base such as sodium hydroxide and potassium hydroxide, or the corresponding amine which is present in excess. The preferred reaction temperature is in the range of 0°-50° C. The preferred solvents are the above organic base, water or organic solvents such as chloroform, tetrahydrofuran and benzene.

The effects of the various compounds of this invention as the preventive and therapeutic treatments for regressive disorders of the central nervous system were assessed by the following test. A mouse fibroblast cell line, L-M cells (ATCC, CCLI, 2) was used which was described in Y. Furukawa et al., J. Biol. Chem., 261, 6039 (1986). Concentration of NGF produced and secreted in the presence of the compound of this invention was measured by the highly sensitive ELISA method. The concentration of NGF was also measured in a system using astroglial cells which were considered as a major source for the production and secretion of NGF in the central nervous system. As shown below in detail in the examples, it has been found that the compound of this invention has an extremely high ability for promoting the production and secretion of NGF. As a result, it has been confirmed that the compounds of this invention may be useful as preventive and therapeutic preparations effective for regressive disorders in the central nervous system in general and SDAT in particular.

When a compound of this invention is used as the active ingredient in preventive or therapeutic pharmaceutical composition or preparation for regressive disorders of the central nervous system, dose and formulation are naturally different depending upon the physical properties of the particular compound, symptoms of the patient and other factors. In oral administration, a suggested dose for an adult is 50–1000 mg a day and may be given as a single dose or in divided doses in the form of tablets, granules, powders, suspensions or capsules. In non-oral administration, a dose of 1–100 mg may be given as a single dose or in divided doses in the form of injections, suppositories of isotonic solutions for infusion.

For example, in preparing tablets, crystal-line cellulose, light anhydrous silicic acid and the like are used for adsorbents, and corn starch, lactose, calcium phosphate, magnesium stearate and the like are used for excipients. In preparing injections, the compound of this invention is used as an aqueous solution, an aqueous lyophobic solution in cotton seed oil, corn oil, peanut oil, olive oil etc. and also as an emulsion obtained by using surface active agents such as HCO-60 (hydrogenated caster oil, NIKKO CHEMICALS' trade name)

EXAMPLES

The present invention will hereinafter be illustrated in detail with respect to the following examples; however, these examples are not to be construed as limiting the scope of the invention.

Preparation Example 1 a) N-Acetyl-3,4-diacetoxyphenethylamine

After dissolving 2.5 g of dopamine into 10 ml of pyridine, 2.7 g of triethylamine was added to the solution.

Then 8 g of acetic anhydride was added and the resultant mixture was reacted with stirring at 60°–70° C. for an hour. The reaction mixture thus obtained was poured into 200 ml of ice water, added with 50 ml of a 2.5N aqueous sodium hydroxide solution and extracted with 100 ml of chloroform. The chloroform layer was washed three times with 30 ml portions of a 2N aqueous hydrochloric acid solution, dried over anhydrous sodium sulfate. After distilling off the solvent under reduced pressure, the residue was purified by colum chromatography using silica gel. A solvent mixture of chloroform: methanol=50:1 was used as an eluent. Pure N-acetyl-3,4-diacetoxyphenethylamine was obtained as a colorless oil. The yield was 3.5 g.

NMR δ ppm (CDCl₃): 1.96 (S, 3H), 2.32 (S, 6H), 2.78 (t, 2H), 3.32–3.56 (m, 2H), 6.00 (br, 1H), 7.00–7.16 (m, 3H).

b) N-Acetyl-3,4-dihydroxyphenethylamine

After dissolving 1 g of N-acetyl-3,4-diacetoxyphenethylamine obtained above into 60 ml of methanol, 30 ml of water and 30 ml of a saturated aqueous sodium hydrogen carbonate solution were added under ice cooling and stirred at room temperature for 12 hours. Then a 3N aqueous hydrochloric acid solution was added dropwise under ice cooling to make the reaction mixture weakly acidic. The resultant solution was extracted four times with 50 ml of chloroform. The aqueous layer was further extracted three times with 40 ml of ethyl acetate. Both extracted solutions were dried and the solvents were distilled off. Both residues were combined and purified by column chromatography using silica gel. A mixture of chloroform:methanol=20:1 was used as an eluent. The yield of pure N-acetyl-3,4-dihydroxyphenethylamine was 0.3 g.

NMR δ ppm (DMSO-d₆): 1.78 (S. 3H), 2.30–2.60 (m, 2H), 2.90–3.24 (m, 2H), 6.30–6.68 (m, 3H), 7.76 (t, 1H), 8.50 (br, 2H).

Preparation Example 2

N-Ethyl-3,4-dihydroxyphenethylamine hydrobromide

After dissolving 5 g of homoveratrylamine in 20 ml of pyridine, 5.6 g of acetic anhydride was added and reacted at 65°–70° C. with stirring for 2 hours. The reaction mixture was poured into 150 ml of ice water and then made weakly acidic by adding 50 ml of a 6N aqueous hydrochloric acid solution. The resultant solution was extracted three times with 50 ml of chloroform. The extracted solution was combined, washed with an aqueous sodium hydrogen carbonate solution and dried over anhydrous sodium sulfate. The solvent was distilled off under reduced pressure. Ether was added to the residue and precipitated crystals were filtered. N-acetylhomoveratrylamine having a melting point of 101°–102° C. was obtained as colorless crystals. The yield was 5.7 g.

To a suspension of 0.98 g of lithium aluminum hydride in 50 ml of dried tetrahydrofuran (THF), a solution of 3 g of N-acetylhomoveratrylamin in 25 ml of THF was added dropwise with stirring. After heating for 3 hours under reflux, the reaction mixture was cooled with ice and gradually added dropwise under violent stirring with a solvent mixture composed of 10 ml of water and 10 ml of THF. Insoluble matter was filtered off and the filtrate was concentrated. The residue obtained was dissolved in 50 ml of ethyl acetate, washed twice with water and dried over anhydrous sodium sulfate. After distilling off the solvent under reduced pressure, N-ethyl-homoveratrylamine was obtained as oily product. The yield was 2.3 g.

After dissolving 1.0 g of N-ethyl-homoveratrylamine in a solvent mixture consisting of 6 ml of a 48% aqueous hydrogen bromide solution and 4 ml of acetic acid, the solution was heated at 120°–130° C. with stirring for 5 hours. The solvent was distilled off and the residue was crystallized from ether to obtain 1.2 g of crude crystals. N-Ethyl-3,4-dihydroxyphenethylamine hydrobromide having a melting point of 149°–151° C. was obtained by recrystallizing from isopropyl alcohol. The yield was 0.68 g.

NMR δ ppm (DMSO-d₆): 1.20 (t, 3H), 2.60–3.20 (m, 6H), 6.40–6.80 (m, 3H), 8.50 (m, 4H).

Preparation Example 3

Ethyl 3,4-diacetoxyphenylpropionate (compound No. 47)

a) To a solution of 18.2 g of dihydroxycaffeic acid in 200 ml of ethanol, 1 ml of concentrated sulfuric acid was added. After heating under reflux for 3 hours, ethanol was distilled off under reduced pressure. The residue was dissolved in 100 ml of ethyl acetate, washed with an aqueous sodium hydrogen carbonate solution and then with water, and dried over anhydrous sodium sulfate. After distilling off ethyl acetate under reduced pressure, ethyl 3,4-diacetoxyphenylpropionate having a melting point of 46°–47° C. was obtained. The yield was 19.8 g.

b) To a solution of 2.1 g of ethyl 3,4-diacetoxyphenylpropionate in 10 ml of pyridine, 4.2 g of acetic anhydride was added dropwise. The mixture was heated at 65°–70° C. with stirring for an hour, poured into 100 ml of ice water, neutralized with a 6N aqueous hydrogen chloride solution and extracted with 50 ml of chloroform. The extracted solution was washed with water and dried over anhydrous sodium sulfate. Chloroform was distilled off under reduced pressure. Ethyl 3,4-diacetoxyphenylpropionate was obtained as oily product. The yield was 2.3 g.

NMR δ ppm (CDCl₃): 1.24 (t, 3H), 2.28 (S, 6H), 2.60 (t, 2H), 3.9 (t, 2H), 4.10 (q, 2H), 6.98–7.08 (m, 3H).

Preparation Example 4

N-Methyl-3,4-dihydroxyphenylpropionamide (Compound No. 59)

A mixture of 2 g of ethyl 3,4-diacetoxyphenylpropionate and 2.1 g of a 40% aqueous methylamine solution was heated to 150° C. with stirring for 2 hours in an autoclave. After cooling, the reaction mixture was acidified, extracted three times with 25 ml of ethyl acetate and dried over anhydrous sodium sulfate. After distilling off the solvent under reduced pressure, the residue was purified by column chromatography using silica gel. A solvent mixture of chloroform:methanol=20:1 was used as eluent. Pure N-methyl-3,4-dihydroxyphenylpropionamide thus obtained was 0.35 g.

Melting Point: 117°–118° C.

IR νcm⁻¹ (KBr): 1620, 1600, 1520, 1300, 1270.

NMR δ ppm (DMSO-d₆): 2.1–2.4 (m, 2H), 2.4–2.8 (m, 5H), 6.1–6.6 (m, 3H), 7.56 (br, 1H), 8.44 (br, 2H).

EXAMPLE 1

N-n-Butyl-3,4-dihydroxyphenylpropionamide (Compound No. 84)

A mixture of 5 g of ethyl 3,4-diacetoxyphenylpropionate and 3.5 g of n-butylamine was heated to 150° C. with stirring for 2 hours in an autoclave. After cooling, the reaction mixture was concentrated and the residue was purified by silica gel chromatography. A solvent mixture of chloroform:methanol=20:1 was used as eluent. Pure N-n-butyl-3,4-dihydroxyphenylpropionamide was obtained as colorless viscous oil. The yield was 5.45 g.

NMR $\delta$ ppm (DMSO-$d_6$): 0.88 (t, 3H), 1.00–1.60 (m, 4H), 2.20–2.40 (m, 2H), 2.40–2.80 (m, 2H), 2.80–3.20 (m, 2H), 6.30–6.70 (m, 3H), 7.58 (t, 1H), 8.38 (s, 1H), 8.50 (s, 1H).

EXAMPLE 2

N-n-Butyl-3,4-diacetoxyphenylpropionamide (Compound No. 85)

To a solution of 2.0 g of N-n-butyl-3,4-dihydroxyphenylpropionamide in 10 ml of pyridine, 3.4 g of acetic anhydride was added dropwise and heated to 65°–70° C. with stirring for an hour. The reaction mixture was poured into 100 ml of ice water, neutralized with 25 ml of 6N hydrochloric acid and extracted three times with 50 ml of chloroform. The extracted solution was washed with a saturated aqueous sodium hydrogen carbonate solution and dried over anhydrous sodium sulfate. The solvent was distilled off under reduced pressure. Hexane was added to the residue. The separated crystals were filtered. N-n-Butyl-3,4-diacetoxyphenylpropionamide thus obtained was 2.3 g.

Melting Point: 71°–73° C.

NMR $\delta$ ppm (CDCl$_3$): 0.88 (t, 3H), 1.00–1.60 (m, 4H), 2.24 (s, 6H), 2.20 2.48 (m, 2H), 2.70–3.28 (m, 4H), 5.60 (br, 1H), 7.00 (m, 3H).

EXAMPLE 3

N-n-Pentyl-3,4-dihydroxyphenylpropionamide (Compound No. 86)

Ethyl 3,4-diacetoxyphenylpropionate and n-pentylamine were used in the procedure described in Example 1, to obtain N-n-pentyl-3,4-dihydroxyphenylpropionamide as an oily product.

NMR $\delta$ ppm (CDCl$_3$): 0.70–1.00 (m, 3H), 1.00–1.60 (m, 6H), 2.30–2.60 (m, 2H), 2.60–3.00 (m, 2H), 3.00–3 30 (m, 2H), 5.70 (br, 1H), 6.40–6.90 (m, 3H), 6.00–8.00 (br, 2H).

EXAMPLE 4

N-n-Hexyl-3,4-dihydroxyphenylpropionamide (Compound No. 87)

Ethyl 3,4-diacetoxyphenylpropionate and n-hexylamine were used to obtain N-n-Hexyl-3,4-dihydroxyphenylpropionamide by carrying out the same procedures as described in Example 1.

Melting point: 69°–70° C.

NMR $\delta$ ppm (DMSO-$d_6$): 0.80–1.00 (m, 3H), 1.26 (s, 10H), 2.16–2.48 (m, 2H), 2.80–3.20 (m, 2H), 6.36–6.70 (m, 3H), 7.64–7.84 (m, 1H), 8.60 (br, 2H).

EXAMPLE 5

N-n-Hexyl-3,4-diacetoxyphenylpropionamide (Compound No. 88)

N-n-Hexyl-3,4-dihydroxyphenylpropionamide was used to obtain N-n-Hexyl-3,4-diacetoxyphenylpropionamide by carrying out the same procedures as described in Example 2.

Melting point: 70°–72° C.

NMR $\delta$ ppm (CDCl$_3$): 0.80–1.00 (m, 3H), 1.00–1.60 (m, 10H), 2.26 (s, 6H), 2.80–3.30 (m, 4H), 5.70 (br, 1H), 7.00–7.20 (m, 3H).

EXAMPLE 6

N-Lauryl-3,4-dihydroxyphenylpropionamide (Compound No. 89)

Ethyl 3,4-diacetoxyphenylpropionate and laurylamine were used to obtain N-Lauryl-3,4-dihydroxyphenylpropionamide by carrying out the same procedures as described in Example 1.

Melting point: 100°–102° C.

NMR $\delta$ ppm (DMSO-$d_6$): 0.80–1.00 (m, 3H), 1.24 (s, 22H), 2.20–2.48 (m, 2H), 2.90–3.20 (m, 2H), 6.40–6.76 (m, 3H), 7.72 (br, 1H), 8.40–8.80 (m, 2H).

EXAMPLE 7

N-n-Butyl-N-methyl-3,4-dihydroxyphenylpropionamide (Compound No. 90)

Ethyl 3,4-diacetoxyphenylpropionate and N-methyl-n-butylamine were used to obtain N-n-Butyl-N-methyl-3,4-dihydroxyphenylpropionamide by carrying out the same procedures as described in Example 1.

Melting point: 96°–98° C.

NMR $\delta$ ppm (CDCl$_3$): 0.38–0.80 (m, 3H), 0.80–1.40 (m, 4H), 2.03–2.53 (m, 4H), 2.53–2.80 (m, 3H), 2.80–3.33 (m, 2H), 6.06–6.70 (m, 3H), 6.70–7.53 (br, 2H).

EXAMPLE 8

N-Stearyl-3,4-dihydroxyphenylpropionamide (Compound No. 91)

Ethyl 3,4-diacetoxyphenylpropionate and stearylamine were used to obtain N-Stearyl-3,4-dihydroxyphenylpropionamide by carrying out the same procedures as described in Example 1.

Melting point: 100°–102° C.

NMR $\delta$ ppm (DMSO-$d_6$): 0.80–1.00 (m, 3H), 1.24 (s, 30H), 2.10–2.40 (m, 4H), 2.40–2.60 (m, 2H), 2.80–3.10 (m, 2H), 6.30–6.68 (m, 3H), 7.70 (br, 1H), 8.50 (s, 1H), 8.70 (s, 1H).

EXAMPLE 9

N,N-Di-n-hexyl-3,4-dihydroxyphenylpropionamide (Compound No. 92)

Ethyl 3,4-diacetoxyphenylpropionate and di-n-hexylamine were used to obtain N,N-Di-n-hexyl-3,4-dihydroxyphenylpropionamide by carrying out the same procedures as described in Example 1, as an oily product.

NMR $\delta$ ppm (CDCl$_3$): 0.60–1.00 (m, 6H), 1.00–1.60 (m, 16H), 2.40–3.00 (m, 4H), 3.00–3.40 (m, 4H), 6.10–7.00 (m, 5H).

EXAMPLE 10

N-Cyclohexyl-3,4-dihydroxyphenylpropionamide (Compound No. 93)

Ethyl 3,4-diacetoxyphenylpropionate and cyclohexylamine were used to obtain N-Cyclohexyl-3,4-dihydroxyphenylpropionamide by carrying out the same procedures as described in Example 1 as an fatty product.

NMR $\delta$ ppm (CDCl$_3$): 0.10–2.00 (m, 11H), 2.20–2.60 (m, 2H), 2.60–2.90 (m, 2H), 5.40–5.60 (m, 1H), 6.00–7.00 (m, 3H), 8.10 (br, 1H).

EXAMPLE 11

N-Methyl N-benzyl-3,4-dihydroxyphenylpropionamide (Compound No. 94)

Ethyl 3,4-diacetoxyphenylpropionate and N-methylbenzylamine were used to obtain N-Methyl-N-benzyl-3,4-dihydroxyphenylpropionamide by carrying out the same procedures as described in Example 1.

Melting point: 107°–109° C.

NMR $\delta$ ppm (CDCl$_3$): 2.40–3.00 (m, 7H), 4.50 (s, 2H), 6.40–7.80 (m, 10H).

EXAMPLE 12

N-Phenyl-3,4-dihydroxyphenylpropionamide (Compound No. 95)

Ethyl 3,4-diacetoxyphenylpropionate and aniline were used to obtain N-Phenyl-3,4-dihydroxyphenylpropionamide by carrying out the same procedures as described in Example 1 as an oily product.

NMR $\delta$ ppm (DMSO-d$_6$): 2.40–2.90 (m, 4H), 6.30–6.80 (m, 3H), 6.80–7.70 (m, 5H), 8.50 (br, 2H), 9.76 (s, 1H).

EXAMPLE 13

N-Adamantyl-3,4-dihydroxyphenylpropionamide (Compound No. 96)

Ethyl 3,4-diacetoxyphenylpropionate and 1-aminoadamantane were used to obtain N-Adamantyl-3,4-dihydroxyphenylpropionamide by carrying out the same procedures as described in Example 1.

Melting point: 213°–215° C.

NMR $\delta$ ppm (DMSO-d$_6$): 1.60 (m, 6H), 1.80–2.10 (m, 8H), 2.10–2.30 (m, 2H), 2.40–2.70 (m, 3H), 6.30–6.60 (m, 3H), 8.40–8.80 (br, 2H).

EXAMPLE 14

N-[3-(3,4-Dihydroxyphenyl)propionyl]piperidine (Compound No. 97)

A mixture of 4.2 g of ethyl 3,4-diacetoxyphenylpropionate and 2.6 g of piperidine was heated to 150° C. with stirring for 4 hours in an autoclave. After cooling, the reaction mixture was concentrated. The residue was purified by column chromatography using silica gel. A solvent mixture of chloroform:methanol = 10:1 was used as eluent. The corresponding fraction was concentrated. The resultant residue was crystallized from a solvent mixture of hexane and ether. The separated crystals were filtered. Pure N-[3-(3,4-Dihydroxyphenyl)propionyl]piperidine was obtained as colorless crystals. The yield was calculated as 4.3 g.

Melting point: 114°–115° C.

NMR $\delta$ ppm (DMSO-d$_6$): 1.2–1.6 (br, 6H), 2.3–2.7 (m, 4H), 3.2–3.5 (m, 4H), 6.25–6.55 (m, 3H), 8.5 (br, 2H).

EXAMPLE 15

N-[3-(3,4-Dihydroxyphenyl)propionyl]pyrrolidine (Compound No. 98)

Ethyl 3,4-diacetoxyphenylpropionate and pyrrolidine were used to obtain N-[3-(3,4-Dihydroxyphenyl)propionyl]pyrrolidine by carrying out the same procedures as described in Example 14.

Melting point: 172°–173° C.

NMR $\delta$ ppm (DMSO-d$_6$): 1.50–2.00 (m, 4H), 2.20–2.80 (m, 4H), 3.10–3.40 (m, 4H), 6.30–6.70 (m, 3H), 8.50 (br, 1H).

EXAMPLE 16

N-[3-(3,4-Dihydroxyphenyl)propionyl]morpholine (Compound No. 99)

Ethyl 3,4-diacetoxyphenylpropionate and morpholine were used to obtain N-[3-(3,4-Dihydroxyphenyl)propionyl]morpholine by carrying out the same procedures as described in Example 14.

Melting point: 211°–213° C.

NMR $\delta$ ppm (DMSO-d$_6$): 2.4–2.7 (m, 4H), 3.2–3.6 (m, 8H), 6.25–6.60 (m, 3H), 8.40 (s, 1H), 8.48 (s, 1H).

EXAMPLE 17

N-Methyl-N'-[3-(3,4-dihydroxyphenyl)propionyl]piperazine (Compound No. 100)

3,4-Dihydroxyphenylpropionic acid ethyl ester and N-methylpiperazine were used to obtain N-Methyl-N'-[3-(3,4-dihydroxyphenyl)propionyl]piperazine by carrying out the same procedures as described in Example 14.

Melting point: 190°–193° C.

NMR $\delta$ ppm (DMSO-d$_6$): 2.00–2.40 (m, 7H), 2.40–2.80 (m, 3H), 3.20–3.60 (m, 5H), 6.40–6.70 (m, 3H), 8.60 (br, 2H).

EXAMPLE 18

N-Benzyl-N'-[3-(3,4-dihydroxyphenyl)propionyl]piperazine (Compound No. 101)

Ethyl 3,4-diacetoxyphenylpropionate and N-benzylpiperazine were used to obtain N-Benzyl-N'-[3-(3,4-dihydroxyphenyl)propionyl]piperazine by carrying out the same procedures as described in Example 14.

Melting point: 178°–180° C.

NMR $\delta$ ppm (DMSO-d$_6$): 2.20–2.40 (m, 4H), 2.40–2.70 (m, 4H), 3.20–3.60 (m, 6H), 6.30–6.80 (m, 3H), 7.20–7.56 (m, 4H), 8.56 (s, 2H).

EXAMPLE 19

N-Diphenylmethyl-N'-[3-(3,4-dihydroxyphenyl)propionyl]piperazine (Compound No. 102)

Ethyl 3,4-diacetoxyphenylpropionate and N-diphenylmethylpiperazine were used to obtain N-Diphenylmethyl-N'-[3-(3,4-dihydroxyphenyl)propionyl]piperazine by carrying out the same procedures as described in Example 14.

Melting point: 163°–164° C.

NMR δ ppm (CDCl₃): 2.00–3.00 (m, 8H), 3.10–3.70 (m, 4H), 4.12 (s, 1H), 6.00–7.60 (m, 13H).

EXAMPLE 20

N-[3-(3,4-dihydroxyphenyl)propionyl]-L-proline methyl ester (Compound No. 103)

(1) To a solution of 2 g of 3,4-diacetylphenylpropionic acid in 10 ml of chloroform, 8.9 g of thionyl chloride was added and heated to 50° C. with stirring for 2 hours. The solvent was distilled off under reduced pressure. The residue thus obtained was crude 3,4-diacetylphenylpropionyl chloride. The yield was 2.1 g. The crude propionyl chloride was used for the next reaction without further purification.

(2) To a suspension of 1.49 g of L-proline methyl ester in 15 ml of chloroform, 3 g of triethylamine was added dropwise. The propionyl chloride obtained in (1) was dissolved in 7 ml of chloroform and added dropwise to the above mixture under ice cooling. The resultant mixture was allowed to stand overnight and heated to 50° C. with stirring for an hour. After cooling, the reaction mixture was poured into 10 ml of ice water. The chloroform layer was separated, washed twice with 25 ml of one N hydrochloric acid and further washed once with an aqueous sodium chloride solution. The resultant chlororform solution was dried over anhydrous sodium sulfate and concentrated. The residue was purified by column chromatography using silica gel. A solvent mixture of chloroform:methanol = 50:1 was used as eluent. N-[3-(3,4-Dihydroxyphenyl)propionyl]-L-proline methyl ester was obtained as colorless oily product. The yield was 1.25 g.

NMR δ ppm (CDCl₃): 1.60–2.40 (m, 4H), 2.12 (s, 3H), 2.30 (s, 3H), 2.40–3.10 (m, 4H), 3.72 (s, 3H), 3.20–3.90 (m, 2H), 4.32–4.50 (m, 1H), 6.60–7.20 (m, 3H).

(3) To a solution of 1.0 g of N-[3-(3,4-diacetoxyphenyl)propionyl]-L-proline methyl ester in 5 ml of methanol, 10 ml of a 5% aqueous ammonia solution was added under ice cooling, and stirred for an hour. The reaction mixture was then acidified with 6N hydrochloric acid under ice cooling and extracted twice with chloroform. The chloroform solution was dried over anhydrous sodium sulfate. N-[3-(3,4-diacetoxyphenyl)-propionyl]-L-proline methyl ester was obtained after distilling off chloroform as a colorless oily product. The yield was 0.7 g.

NMR δ ppm (CDCl₃): 1.60–2.30 (m, 4H), 2.30–3.00 (m, 4H), 3.00–3.60 (m, 2H), 3.64 (s, 3H), 4.40–4.60 (m, 1H), 6.40–6.80 (m, 3H), 6.90 (br, 1H), 7.60 (br, 1H).

EXAMPLE 21

Ethyl N-[3-(3,4-dihydroxyphenyl)propionyl]nipecotinate (Compound No. 104)

The same procedures as described in Example 20 were carried out except that nipecotic acid ethyl ester hydrochloride was used in place of L-proline methyl ester hydrochloride.

Thus N-[3-(3,4-dihydroxyphenyl)propionyl]nipecotic acid ethyl ester was obtained as a colorless oily product.

NMR δ ppm (CDCl₃): 1.20–1.48 (m, 3H), 1.46–2.40 (m, 5H), 2.40–3.54 (m, 6H), 3.54–4.68 (m, 4H), 6.50–7.20 (m, 4H), 7.66 (br, 1H).

EXAMPLE 22

Acute toxicity

A group of male ddy 10 mice 5-weeks old was used for the acute toxicity test. The test sample was prepared by suspending the test compound in 0.5% aqueous Tween 80. The test compound was administered by intraperitoneal injection. Numbers of deaths were counted after one and four days, and an $LD_{50}$ value was calculated from these numbers.

None of the compounds tested had a $LD_{50}$ value of at least 1000 mg/kg. That is, acute toxicity was extremely low.

EXAMPLE 23

Promoting activity for the production and secretion of NGF in mouse L-M cells

This experiment was performed according to the procedures of Y. Furukawa et al. which is described in J. Biol. Chem., 261, 6039–6047 (1986).

Mouse L-M cells were precultured in Medium 199 (a product of Gibco Co.) supplemented with 0.5% peptone, and then innoculated in a 24-well cultivation plate having a well surface area of 2.1 cm² (a product of Falcon Co.) at a cell density of about $3 \times 10^4$ cells/well. The medium was cultured for 3 days at a temperature of 37° C. After completing the confluency (about 10⁶ cells/well), the medium was changed to Medium 199 (0.5 ml/well) containing 0.5% bovine serum albumin (Fraction V, a product of Armour Co.). The sample of the derivative tested is contained in the medium at a prescribed concentration as illustrated in the Tables. NGF concentration in the medium after cultivating for 24 hours was determined according to high sensitivity ELISA [S. Furukawa et al., J. Nuurochem., 40, 734–744 (1983)]. Data are expressed as fold increase in NGF content of the medium over that cultivated in the absence of the derivative to be tested. The lower detection limit of ELISA is 0.25 pg/ml and the NGF content of control medium is normally 50–200 pg/0.5 ml/well. Data are presented as the mean of four determinations. The results are illustrated in Tables 1–5.

EXAMPLE 24

Promoting activity for the production and secretion of NGF in mouse brain astroglial cells The experiment was performed by inducing astroglial cells from the mouse forebrain to a culture system according to the procedures of S. Furukawa et al. which is described in Biochem. Biophys. Res. Commun., 136, 57–63 (1986).

Forebrains of 8-days old mice were dissected out and cut into small pieces. The pieces were washed with calcium- and magnesium-free phosphate-buffered saline (hereinafter abbreviated as PBS), treated with 0.25% trypsin containing PBS at 37° C. for 30 minutes and triturated with a Pasteur pipet to give a suspension. Cells and cell clumps were recovered by centrifugation at 200 xg for 5 minutes. They were cultured in Dulbecco modified Eagle's medium (a product of Gibco Co. hereinafter abbreviated as DMEM) containing 10% fetal calf serum, 50 μ units/ml of penicillin, and 50 μg/ml of streptomycin, for 10 to 14 days with medium changes every 3 days. After completing confluency, the cells were dissociated by trypsin treatment and recultured in new culture flasks. This procedure was repeated further twice and more. The culture became a uniform cell cluster. The cell cluster for use in this invention can be stained not less than 97% in accordance with the PAP staining method (peroxidase/antioxidase staining method) using anti-human glial fibrillar acidic protein (GFAP) rabbit antiserum. The cells will hereinafter be referred to as astroglial cells.

Astroglial cells were innoculated in 24-well plates having a well surface area of 2.1 cm$^2$ (a product of Falcon Co.) at a cell density of about $3 \times 10^4$ cells/well and cultured for 3 days in DMEM medium supplemented with 10% of fetal calf serum. After completing confluency about ($10^7$ cells/well), the medium was changed to DMEM medium (0.5 ml/well) supplemented with 0.5% of bovine serum albumin (fraction V) and cultured for 3 days. The culture was further continued with medium changes every 3 days. After cells were practically synchronized in the quiscent stage, the medium was changed to 0.5 ml of the same medium and containing a prescribed concentration of test sample as illustrated in the Tables. NGF in the medium after cultivating for 24 hours was determined by the ELISA as mentioned above. Data are expressed as fold increase in NGF content over that in the absence of the test sample. The lower detection limit of the ELISA is 0.25 pg/ml and the NGF content of control medium was normally 1–10 pg/0.5 ml/well. Data are presented as the mean of four determinations. The results are illustrated in Tables 1–5.

TABLE 1

Promoting activity of compound having the following formula for the production and secretion of NGF in mouse L-M cells.

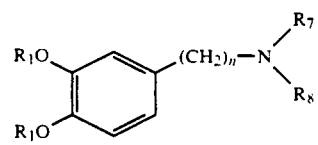

| Compound No. | Substituent | | | | Sample Concentration (mM) | NGF Concentration (ng/well) | NGF Increase Ratio |
|---|---|---|---|---|---|---|---|
| | $R_1$ | $R_7$ | $R_8$ | n | | | |
| | | Control | | | 0 | 0.33 | 1.00 |
| 1 | H | —COCH$_3$ | H | 2 | 0.2 | 3.05 | 9.24 |
| 2 | H | —COCH$_2$CH$_3$ | H | 2 | 0.2 | 3.10 | 9.39 |
| 3 | H | —COCH$_2$CH$_2$CH$_3$ | H | 2 | 0.2 | 3.18 | 9.64 |
| 4 | H | —COCH$_3$ | H | 1 | 0.2 | 2.60 | 7.88 |
| 5 | H | —COCH$_2$CH$_3$ | H | 1 | 0.2 | 2.75 | 8.33 |
| 6 | H | —COCH$_2$CH$_2$CH$_3$ | H | 1 | 0.2 | 2.95 | 8.94 |
| 7 | H | —COCH$_3$ | H | 3 | 0.2 | 2.81 | 8.52 |
| 8 | H | —COCH$_2$CH$_3$ | H | 3 | 0.2 | 2.90 | 8.79 |
| 9 | H | —COCH$_2$CH$_2$CH$_3$ | H | 3 | 0.2 | 2.75 | 8.33 |
| 10 | H | —COCH$_3$ | —CH$_3$ | 2 | 0.2 | 3.20 | 9.70 |
| 11 | H | —COCH$_2$CH$_3$ | —CH$_3$ | 2 | 0.2 | 3.32 | 10.06 |
| 12 | H | —COCH$_2$CH$_2$CH$_3$ | —CH$_3$ | 2 | 0.2 | 3.02 | 9.15 |
| 13 | —COCH$_3$ | —COCH$_3$ | H | 2 | 0.2 | 4.03 | 12.21 |
| 14 | —COCH$_3$ | —COCH$_2$CH$_3$ | H | 2 | 0.2 | 3.49 | 10.58 |
| 15 | —COCH$_3$ | —COCH$_2$CH$_2$CH$_3$ | H | 2 | 0.2 | 2.95 | 8.94 |
| 16 | —COCH$_3$ | —COCH$_3$ | H | 1 | 0.2 | 2.72 | 8.24 |
| 17 | —COCH$_3$ | —COCH$_3$ | H | 3 | 0.2 | 2.85 | 8.64 |
| 18 | —COCH$_3$ | —COCH$_3$ | —CH$_3$ | 2 | 0.2 | 3.95 | 11.97 |
| 19 | H | —CH$_2$CH$_3$ | H | 2 | 0.2 | 3.50 | 10.61 |
| 20 | H | —CH$_2$CH$_2$CH$_3$ | H | 2 | 0.2 | 3.62 | 10.97 |
| 21 | H | —CH$_2$CH$_2$CH$_2$CH$_3$ | H | 2 | 0.2 | 3.80 | 11.52 |
| 22 | H | —CH$_3$ | H | 1 | 0.2 | 2.97 | 9.00 |
| 23 | H | —CH$_2$CH$_3$ | H | 1 | 0.2 | 3.08 | 9.33 |
| 24 | H | —CH$_2$CH$_2$CH$_3$ | H | 1 | 0.2 | 2.94 | 8.91 |
| 25 | H | —CH$_2$CH$_2$CH$_2$CH$_3$ | H | 1 | 0.2 | 2.91 | 8.82 |
| 26 | H | —CH$_3$ | H | 3 | 0.2 | 2.84 | 8.61 |
| 27 | H | —CH$_2$CH$_3$ | H | 3 | 0.2 | 2.89 | 8.76 |
| 28 | H | —CH$_2$CH$_2$CH$_3$ | H | 3 | 0.2 | 2.79 | 8.45 |
| 29 | H | —CH$_2$CH$_2$CH$_2$CH$_3$ | H | 3 | 0.2 | 2.88 | 8.73 |
| 30 | —COCH$_3$ | —CH$_3$ | —CH$_3$ | 2 | 0.2 | 3.80 | 11.52 |
| 31 | —COCH$_3$ | —CH$_2$CH$_3$ | —CH$_3$ | 2 | 0.2 | 3.76 | 11.39 |
| | | Comparative Example | | | | | |
| Comparative compound | H | H | H | 2 | 0.2 | 1.30 | 3.94 |

TABLE 2

Promoting activity of compound having the following formula for the production and secretion of NGF in mouse L-M cells.

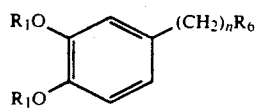

| Compound No. | Substituent R₁ | R₆ | n | Sample Concentration (mM) | NGF Concentration (ng/well) | NGF Increase Ratio |
|---|---|---|---|---|---|---|
| | | Control | | 0 | 0.34 | 1.00 |
| 34 | H | —COOCH₃ | 2 | 0.2 | 1.97 | 5.79 |
| 35 | H | —COOCH₂CH₃ | 2 | 0.2 | 1.98 | 5.82 |
| 36 | H | —COOCH₂CH₂CH₃ | 2 | 0.2 | 1.88 | 5.53 |
| 37 | H | —COOCH₂CH₂CH₂CH₃ | 2 | 0.2 | 1.85 | 5.44 |
| 38 | H | —COOCH₃ | 1 | 0.2 | 1.63 | 4.79 |
| 39 | H | —COOCH₂CH₃ | 1 | 0.2 | 1.78 | 5.24 |
| 40 | H | —COOCH₂CH₂CH₃ | 1 | 0.2 | 1.84 | 5.41 |
| 41 | H | —COOCH₂CH₂CH₂CH₃ | 1 | 0.2 | 1.79 | 5.26 |
| 42 | H | —COOCH₃ | 3 | 0.2 | 1.81 | 5.32 |
| 43 | H | —COOCH₂CH₃ | 3 | 0.2 | 1.88 | 5.53 |
| 44 | H | —COOCH₂CH₂CH₃ | 3 | 0.2 | 1.91 | 5.62 |
| 45 | H | —COOCH₂CH₂CH₂CH₃ | 3 | 0.2 | 1.84 | 5.41 |
| 46 | CH₃CO— | —COOCH₃ | 2 | 0.2 | 2.01 | 5.91 |
| 47 | CH₃CO— | —COOCH₂CH₃ | 2 | 0.2 | 2.14 | 6.29 |
| 48 | CH₃CO— | —COOCH₂CH₂CH₃ | 2 | 0.2 | 2.13 | 6.26 |
| 49 | CH₃CO— | —COOCH₂CH₂CH₂CH₃ | 2 | 0.2 | 2.14 | 6.29 |
| 50 | CH₃CO— | —COOCH₃ | 1 | 0.2 | 1.73 | 5.09 |
| 51 | CH₃CO— | —COOCH₂CH₃ | 1 | 0.2 | 1.98 | 5.82 |
| 52 | CH₃CO— | —COOCH₂CH₂CH₃ | 1 | 0.2 | 1.88 | 5.53 |
| 53 | CH₃CO— | —COOCH₂CH₂CH₂CH₃ | 1 | 0.2 | 1.63 | 4.79 |
| 54 | CH₃CO— | —COOCH₃ | 3 | 0.2 | 1.88 | 5.53 |
| 55 | CH₃CO— | —COOCH₂CH₃ | 3 | 0.2 | 1.98 | 5.82 |
| 56 | CH₃CO— | —COOCH₂CH₂CH₃ | 3 | 0.2 | 1.73 | 5.09 |
| 57 | CH₃CO— | —COOCH₂CH₂CH₂CH₃ | 3 | 0.2 | 1.81 | 5.32 |
| 58 | H | —CONH₂ | 2 | 0.2 | 1.88 | 5.53 |
| 59 | H | —CONHCH₃ | 2 | 0.2 | 1.91 | 5.62 |
| 60 | H | —CONHCH₂CH₃ | 2 | 0.2 | 1.84 | 5.41 |
| 61 | H | —CONHCH₂CH₂CH₃ | 2 | 0.2 | 2.01 | 5.91 |
| 62 | H | —CONH₂ | 1 | 0.2 | 1.63 | 4.79 |
| 63 | H | —CONHCH₃ | 1 | 0.2 | 1.98 | 5.82 |
| 64 | H | —CONHCH₂CH₃ | 1 | 0.2 | 1.81 | 5.32 |
| 65 | H | —CONHCH₂CH₂CH₃ | 1 | 0.2 | 1.77 | 5.21 |
| 66 | H | —CONHCH₂CH₂CH₂CH₃ | 1 | 0.2 | 1.99 | 5.85 |
| 67 | H | —CONH₂ | 3 | 0.2 | 1.69 | 4.97 |
| 68 | H | —CONHCH₃ | 3 | 0.2 | 1.73 | 5.09 |
| 69 | H | —CONHCH₂CH₃ | 3 | 0.2 | 1.88 | 5.53 |
| 70 | H | —CONHCH₂CH₂CH₃ | 3 | 0.2 | 1.83 | 5.38 |
| 71 | H | —CONHCH₂CH₂CH₂CH₃ | 3 | 0.2 | 1.83 | 5.71 |
| 72 | H | —CON(CH₃)₂ | 2 | 0.2 | 1.94 | 5.91 |
| 73 | CH₃CO— | —CONH₂ | 2 | 0.2 | 2.01 | 5.68 |
| 74 | CH₃CO— | —CONHCH₂CH₃ | 2 | 0.2 | 1.93 | 5.85 |
| 75 | CH₃CO— | —CONH₂ | 1 | 0.2 | 2.03 | 5.53 |
| 76 | CH₃CO— | —CONHCH₂CH₃ | 1 | 0.2 | 1.88 | 5.47 |
| 77 | CH₃CO— | —CONHCH₂CH₂CH₂CH₃ | 1 | 0.2 | 1.86 | 5.26 |
| 78 | CH₃CO— | —CONH₂ | 3 | 0.2 | 1.79 | 4.94 |
| 79 | CH₃CO— | —CONHCH₂CH₃ | 3 | 0.2 | 1.82 | 5.35 |
| 80 | CH₃CO— | —CONHCH₂CH₂CH₂CH₃ | 3 | 0.2 | 1.95 | 5.74 |
| 81 | CH₃CO— | —CON(CH₃)₂ | 2 | 0.2 | 1.96 | 5.76 |

TABLE 3

Promoting activity of compound having the following formula for the production and secretion of NGF in mouse brain astroglial cells.

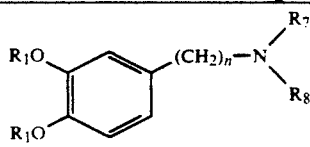

| Compound No. | Substituent R₁ | R₇ | R₈ | n | Sample Concentration (mM) | NGF Concentration (ng/well) | NGF Increase Ratio |
|---|---|---|---|---|---|---|---|
| | | Control | | | 0 | 42.3 | 1.00 |
| 1 | H | —COCH₃ | H | 2 | 0.4 | 208.8 | 4.94 |
| 3 | H | —COCH₂CH₂CH₃ | H | 2 | 0.2 | 155.0 | 3.66 |
| 7 | H | —COCH₃ | H | 3 | 0.4 | 188.5 | 4.46 |

TABLE 3-continued

Promoting activity of compound having the following formula for the production and secretion of NGF in mouse brain astroglial cells.

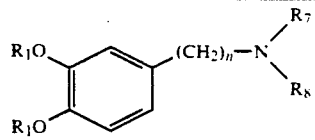

| Compound No. | Substituent $R_1$ | $R_7$ | $R_8$ | n | Sample Concentration (mM) | NGF Concentration (ng/well) | NGF Increase Ratio |
|---|---|---|---|---|---|---|---|
| 10 | H | —COCH$_3$ | —CH$_3$ | 2 | 0.4 | 205.2 | 4.85 |
| 12 | H | —COCH$_2$CH$_2$CH$_3$ | —CH$_3$ | 2 | 0.4 | 206.7 | 4.89 |
| 13 | —COCH$_3$ | —COCH$_3$ | H | 2 | 0.4 | 198.8 | 4.70 |
| 15 | —COCH$_3$ | —COCH$_2$CH$_2$CH$_3$ | H | 2 | 0.2 | 158.2 | 3.74 |
| 17 | —COCH$_3$ | —COCH$_3$ | H | 3 | 0.2 | 180.6 | 4.27 |
| 19 | H | —CH$_2$CH$_3$ | H | 2 | 0.4 | 176.3 | 4.17 |
| 21 | H | —CH$_2$CH$_2$CH$_2$CH$_3$ | H | 2 | 0.4 | 207.5 | 4.91 |
| 32 | H | —CH$_2$CH$_2$CH$_2$CH$_3$ | —CH$_3$ | 2 | 0.4 | 203.8 | 4.82 |
| 33 | —COCH$_3$ | —CH$_2$CH$_2$CH$_2$CH$_3$ | —CH$_3$ | 2 | 0.4 | 200.6 | 4.74 |
| 26 | H | —CH$_3$ | H | 3 | 0.4 | 176.5 | 4.17 |
| 29 | H | —CH$_2$CH$_2$CH$_2$CH$_3$ | H | 3 | 0.4 | 180.3 | 4.26 |

TABLE 4

Promoting activity of compound having the following formula for the production and secretion of NGF in mouse brain astroglial cells.

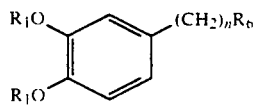

| Compound No. | Substituent $R_1$ | $R_6$ | n | Sample Concentration (mM) | NGF Concentration (ng/well) | NGF Increase Ratio |
|---|---|---|---|---|---|---|
| 35 | H | —COOCH$_2$CH$_3$ | 2 | 0.2 | 200.1 | 4.63 |
| 37 | H | —COOCH$_2$CH$_2$CH$_2$CH$_3$ | 2 | 0.2 | 208.5 | 4.83 |
| 39 | H | —COOCH$_2$CH$_3$ | 1 | 0.2 | 210.1 | 4.86 |
| 43 | H | —COOCH$_2$CH$_3$ | 3 | 0.2 | 198.5 | 4.59 |
| 47 | CH$_3$CO— | —COOCH$_2$CH$_3$ | 2 | 0.4 | 220.8 | 5.11 |
| 49 | CH$_3$CO— | —COOCH$_2$CH$_2$CH$_2$CH$_3$ | 2 | 0.4 | 223.7 | 5.18 |
| 51 | CH$_3$CO— | —COOCH$_2$CH$_3$ | 1 | 0.4 | 194.6 | 4.50 |
| 55 | CH$_3$CO— | —COOCH$_2$CH$_3$ | 3 | 0.4 | 189.7 | 4.39 |
| 58 | H | —CONH$_2$ | 2 | 0.2 | 230.0 | 5.32 |
| 60 | H | —CONHCH$_2$CH$_3$ | 2 | 0.2 | 300.4 | 6.95 |
| 82 | H | —CONHCH$_2$CH$_2$CH$_2$CH$_3$ | 2 | 0.2 | 360.9 | 8.35 |
| 64 | H | —CONHCH$_2$CH$_3$ | 1 | 0.2 | 200.8 | 4.65 |
| 69 | H | —CONHCH$_2$CH$_3$ | 3 | 0.2 | 194.1 | 4.49 |
| 72 | H | —CON(CH$_3$)$_2$ | 2 | 0.2 | 280.6 | 6.50 |
| 74 | CH$_3$CO— | —CONHCH$_2$CH$_3$ | 2 | 0.4 | 282.2 | 6.53 |
| 73 | CH$_3$CO— | —CONH$_2$ | 2 | 0.4 | 330.6 | 7.65 |
| 83 | CH$_3$CO— | —CONHCH$_2$CH$_2$CH$_2$CH$_3$ | 2 | 0.4 | 381.2 | 8.82 |
| 76 | CH$_3$CO— | —CONHCH$_2$CH$_3$ | 1 | 0.4 | 209.1 | 4.84 |
| 79 | CH$_3$CO— | —CONHCH$_2$CH$_3$ | 3 | 0.4 | 197.3 | 4.57 |
| 81 | CH$_3$CO— | —CON(CH$_3$)$_2$ | 2 | 0.4 | 273.5 | 6.33 |

TABLE 5

Promoting activity of compound having the following formula for the production and secretion of NGF in mouse L-M cells and brain astroglial cells.

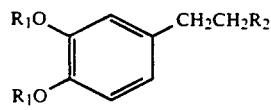

| Compound | | | NGF | | | |
|---|---|---|---|---|---|---|
| | Substituent | | L-M Cell | | Astroglial Cell | |
| No. | $R_1$ | $R_2$ | Concentration (mM) | Concentration (ng/well) | Increase Ratio | Concentration (ng/well) | Increase Ratio |
| 84 | H | —CONH(CH$_2$)$_3$CH$_3$ | 0.4 | 5.39 | 6.2 | 539.5 | 33.1 |
| 85 | CH$_3$CO | —CONH(CH$_2$)$_3$CH$_3$ | 0.4 | 5.92 | 6.8 | 547.7 | 33.6 |
| 86 | H | —CONH(CH$_2$)$_4$CH$_3$ | 0.4 | 5.66 | 6.5 | 493.9 | 30.3 |
| 87 | H | —CONH(CH$_2$)$_5$CH$_3$ | 0.4 | 5.05 | 5.8 | 195.6 | 12.0 |

TABLE 5-continued

Promoting activity of compound having the following formula for the production and secretion of NGF in mouse L-M cells and brain astroglial cells.

$$R_1O-C_6H_3(OR_1)-CH_2CH_2R_2$$

| | Compound Substituent | | Concentration | NGF L-M Cell | | Astroglial Cell | |
|---|---|---|---|---|---|---|---|
| No. | $R_1$ | $R_2$ | (mM) | Concentration (ng/well) | Increase Ratio | Concentration (ng/well) | Increase Ratio |
| 88 | $CH_3CO$ | $-CONH(CH_2)_5CH_3$ | 0.4 | 5.39 | 6.2 | 257.5 | 15.8 |
| 89 | H | $-CONH(CH_2)_{11}CH_3$ | 0.4 | 3.74 | 4.3 | 81.5 | 5.0 |
| 90 | H | $-CON(CH_3)((CH_2)_3CH_3)$ | 0.4 | 5.57 | 6.4 | 489.0 | 30.0 |
| 91 | H | $-CONH(CH_2)_{17}CH_3$ | 0.4 | 3.57 | 4.1 | 84.8 | 5.2 |
| 92 | H | $-CON((CH_2)_5CH_3)_2$ | 0.4 | 4.35 | 5.0 | 143.4 | 8.8 |
| 93 | H | $-CONH-cyclohexyl$ | 0.4 | 5.22 | 6.0 | 161.4 | 9.9 |
| 94 | H | $-CON(CH_3)(CH_2C_6H_5)$ | 0.4 | 4.44 | 5.1 | 84.8 | 5.2 |
| 95 | H | $-CONH-C_6H_5$ | 0.4 | 5.13 | 5.9 | 182.6 | 11.2 |
| 96 | H | $-CONH-adamantyl$ | 0.4 | 4.96 | 5.7 | 293.4 | 18.0 |
| 97 | H | $-CON$(piperidinyl) | 0.4 | 5.39 | 6.2 | 435.7 | 13.7 |
| 98 | H | $-CON$(pyrrolidinyl) | 0.4 | 5.31 | 6.1 | 407.0 | 12.8 |
| 99 | H | $-CON$(morpholinyl) | 0.4 | 4.18 | 4.8 | 165.4 | 5.2 |
| 100 | H | $-CON$(N-methylpiperazinyl) | 0.4 | 4.35 | 5.0 | 260.8 | 8.2 |

TABLE 5-continued

Promoting activity of compound having the following formula for the production and secretion of NGF in mouse L-M cells and brain astroglial cells.

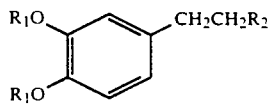

| | Compound | | | NGF | | | |
|---|---|---|---|---|---|---|---|
| | Substituent | | | L-M Cell | | Astroglial Cell | |
| No. | $R_1$ | $R_2$ | Concentration (mM) | Concentration (ng/well) | Increase Ratio | Concentration (ng/well) | Increase Ratio |
| 101 | H | —CON⟨ ⟩NCH₂ph | 0.4 | 4.52 | 5.2 | 305.3 | 9.6 |
| 102 | H | —CON⟨ ⟩NCH(ph)(ph) | 0.4 | 4.44 | 5.1 | 321.2 | 10.1 |
| 103 | H | —CON⟨ ⟩COOCH₃ | 0.4 | 3.74 | 4.3 | 200.3 | 6.3 |
| 104 | H | —CON⟨ ⟩COOC₂H₅ | 0.4 | 4.96 | 5.7 | 248.0 | 7.8 |
| Control | | | 0 | 0.87 | 1.00 | 31.8 | 1.00 |

(1) ph: phenyl group

What is claimed is:

1. A catechol derivative or a pharmaceutically acceptable salt thereof represented by the formula (I):

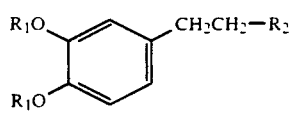 (I)

wherein $R_1$ is a hydrogen atom or an acetyl group and $R_2$ is

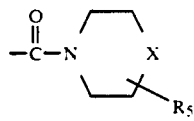

group where $R_5$ is a hydrogen atom, an alkyl group, a benzyl group, or a diphenylmethyl group, and X is a direct bond, oxygen atom, nitrogen atom or a methylene group.

2. A pharmaceutical composition for the treatment of regressive disorders of the central nervous system which comprises as an active ingredient a catechol derivative represented by the formula (II):

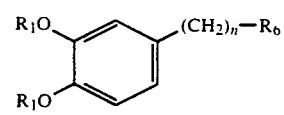 (II)

wherein $R_6$ is a

group where $R_1$ is a hydrogen atom or an acetyl group, $R_5$ is a hydrogen atom, alkyl group, a benzyl group, or a diphenylmethyl group, X is a direct bond, oxygen atom, nitrogen atom, or a methylene group, and n is an integer of 1, 2, or 3 together with a pharmaceutically acceptable carrier or diluent.

3. The catechol derivative of claim 1 in which the derivative is selected from the group consisting of numbered below 97 to 102;

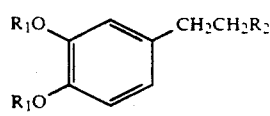

| | Substituent | |
|---|---|---|
| No. | R₁ | R₂ |
| 97 | H |  |
| 98 | H |  |
| 99 | H |  |
| 100 | H | 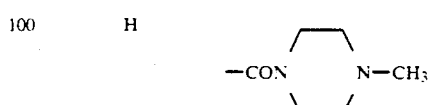 |

-continued

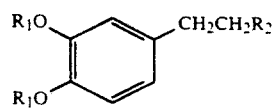

| | Substituent | |
|---|---|---|
| No. | R₁ | R₂ |
| 101 | H | —CON⟨ ⟩NCH₂ph |
| 102 | H | —CON⟨ ⟩NCH(ph)(ph) | ph: phenyl group

4. The pharmaceutical composition of claim 2 containing from 50 to 1,000 mg of the catechol derivative.

5. The pharmaceutical composition of claim 4 in an orally administrable form.

6. The pharmaceutical composition of claim 2 in an injectable form containing from 1 to 100 mg of the catechol derivative.

7. A method of treating regressive disorders of the central nervous system treatable by inducing the production and secretion of nerve growth factor, comprising administering to a person suffering therefrom a nerve growth factor production and secretion therapeutically effective amount of a catechol derivative of claim 1.

8. A method of treating regressive disorders of the central nervous system treatable by inducing the production and secretion of nerve growth factor, comprising administering to a person suffering therefrom a nerve growth factor production and secretion therapeutically effective amount of the pharmaceutical composition of claim 2.

9. The method of claims 7 or 8 in which the amount of catechol derivative administered is from 1 to 1000 mg per day.

* * * * *